(12) United States Patent
Kamiyama et al.

(10) Patent No.: US 10,395,092 B2
(45) Date of Patent: Aug. 27, 2019

(54) PROCESSING DEVICE, PROCESSING METHOD, AND INFORMATION STORAGE DEVICE

(71) Applicant: OLYMPUS CORPORATION, Tokyo (JP)

(72) Inventors: Toshiya Kamiyama, Hachioji (JP); Makoto Kitamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/877,558

(22) Filed: Jan. 23, 2018

(65) Prior Publication Data

US 2018/0150675 A1 May 31, 2018

Related U.S. Application Data

(63) Continuation of application No. PCT/JP2015/071089, filed on Jul. 24, 2015.

(51) Int. Cl.
*G06K 9/00* (2006.01)
*A61B 1/04* (2006.01)
(Continued)

(52) U.S. Cl.
CPC ............ *G06K 9/0014* (2013.01); *A61B 1/04* (2013.01); *A61B 5/00* (2013.01); *G06K 9/00134* (2013.01); *G06K 9/00147* (2013.01); *G06K 9/6214* (2013.01); *G06N 20/00* (2019.01); *G06T 7/0012* (2013.01); *G06T 2207/10024* (2013.01); *G06T 2207/10068* (2013.01);
(Continued)

(58) Field of Classification Search
USPC .................................................. 382/128–134
See application file for complete search history.

(56) References Cited

U.S. PATENT DOCUMENTS

2005/0036668 A1* 2/2005 McLennan ........... G06K 9/4652
382/128
2005/0201599 A1* 9/2005 Matsui .................. G06T 7/0012
382/128

(Continued)

FOREIGN PATENT DOCUMENTS

JP 2000-163396 A 6/2000
JP 2004-295879 A 10/2004
(Continued)

OTHER PUBLICATIONS

International Search Report dated Oct. 27, 2015 issued in PCT/JP2015/071089.

(Continued)

*Primary Examiner* — Alex Kok S Liew
(74) *Attorney, Agent, or Firm* — Scully, Scott, Murphy & Presser, P.C.

(57) ABSTRACT

A processing device includes a processor including hardware. The processor is configured to implement an image acquisition process of acquiring a tissue image obtained by capturing an image of a tissue and a process of determining a property of the tissue image acquired, and setting a plurality of identification criteria for identifying a state of the tissue as a normal state or an abnormal state, based on the tissue image and the property of the tissue image.

25 Claims, 19 Drawing Sheets

(51) Int. Cl.
  *A61B 5/00* (2006.01)
  *G06K 9/62* (2006.01)
  *G06T 7/00* (2017.01)
  *G06N 20/00* (2019.01)

(52) U.S. Cl.
  CPC .............. *G06T 2207/20081* (2013.01); *G06T 2207/30004* (2013.01); *G06T 2207/30024* (2013.01)

(56) References Cited

U.S. PATENT DOCUMENTS

| | | | | |
|---|---|---|---|---|
| 2007/0237372 | A1* | 10/2007 | Chen | G06K 9/6203 382/128 |
| 2008/0075344 | A1* | 3/2008 | Nambu | A61B 6/463 382/131 |
| 2010/0119110 | A1 | 5/2010 | Kanda | |
| 2012/0141002 | A1* | 6/2012 | Urbano | G01S 7/5205 382/131 |

FOREIGN PATENT DOCUMENTS

| | | |
|---|---|---|
| JP | 2005-065856 A | 3/2005 |
| JP | 2005-214682 A | 8/2005 |
| JP | 2005-309920 A | 11/2005 |
| JP | 2009-037565 A | 2/2009 |
| JP | 2010-113616 A | 5/2010 |
| JP | 2011-232303 A | 11/2011 |
| JP | 2013-125322 A | 6/2013 |
| WO | WO 2014/024758 A1 | 2/2014 |

OTHER PUBLICATIONS

Japanese Office Action dated Jul. 2, 2019 in Japanese Patent Application No. 2017-530467.

* cited by examiner

| ORGAN TYPE | COLOR FEATURE AMOUNT | TEXTURE FEATURE AMOUNT | SHAPE FEATURE AMOUNT |
|---|---|---|---|
| STOMACH | ○ | ○ | |
| SMALL INTESTINE | ○ | ○ | |
| LARGE INTESTINE | | | ○ |

| ORGAN TYPE | TARGET | IDENTIFICATION CRITERION |
|---|---|---|
| STOMACH | × | RE-GENERATE |
| SMALL INTESTINE | ○ | CORRECT |
| LARGE INTESTINE | × | RE-GENERATE |

| | | IDENTIFICATION CRITERION | | | |
|---|---|---|---|---|---|
| | | A | B | C | ... |
| ORGAN TYPE | STOMACH | 0.2 | 0.1 | 0.3 | ... |
| | SMALL INTESTINE | 0.9 | 0 | 0.1 | ... |
| | LARGE INTESTINE | 0.5 | 0.1 | 0.1 | ... |
| | ... | ... | ... | ... | ... |

# PROCESSING DEVICE, PROCESSING METHOD, AND INFORMATION STORAGE DEVICE

CROSS REFERENCE TO RELATED APPLICATION

This application is a continuation of International Patent Application No. PCT/JP2015/071089, having an international filing date of Jul. 24, 2015, which designated the United States, the entirety of which is incorporated herein by reference.

BACKGROUND

The present invention relates to a processing device, a processing method, an information storage device, and the like.

In medical sites, a physician acquires a tissue image of a patient (subject), and checks the acquired tissue image to determine whether or not there is an abnormality in a tissue. The number of tissue images acquired might be extremely large, requiring the physician to take a long time to check all of the images.

Thus, in recent years, studies have been made on a processing device for supporting the physician, in diagnosis, by checking and identifying the contents of a great number of tissue images one by one to automatically identify a tissue image including a portion with abnormality and presenting the tissue image to the physician. This automatic identification of the contents of the images is performed as follows. Specifically, an identification criterion is generated in advance through machine learning using learning images provided with true labels in advance. In this condition, the contents of the images acquired by the physician for diagnosis are mechanically identified with the identification criterion, and an identification result is presented to the physician and the like.

The identification criterion is preferably usable for identifying rare cases. In this context, studies have been made on a method including performing successive learning by using images actually acquired in the medical site to update the identification criterion prepared in advance to increase identifiable cases. The mechanical learning for updating the original identification criterion by using new learning data appended with a corrected label is referred to as incremental learning. JP-A-2009-37565 discloses an invention that is a conventional technique related to the incremental learning.

SUMMARY

According to one aspect of the invention, there is provided a processing device comprising:

a processor comprising hardware, the processor being configured to implement:

an image acquisition process of acquiring a tissue image obtained by capturing an image of a tissue; and a process of determining a property of the tissue image acquired, and setting a plurality of identification criteria for identifying a state of the tissue as a normal state or an abnormal state, based on the tissue image and the property of the tissue image.

According to another aspect of the invention, there is provided a processing method comprising:

acquiring a tissue image obtained by capturing an image of a tissue; and determining a property of the tissue image acquired, and setting a plurality of identification criteria for identifying a state of the tissue as a normal state or an abnormal state, based on the tissue image and the property of the tissue image.

According to another aspect of the invention, there is provided a computer-readable storage device with an executable program stored thereon, wherein the program instructs a microprocessor to perform the following steps of;

acquiring a tissue image obtained by capturing an image of a tissue; and determining a property of the tissue image acquired, and setting a plurality of identification criteria for identifying a state of the tissue as a normal state or an abnormal state, based on the tissue image and the property of the tissue image.

DESCRIPTION OF EXEMPLARY EMBODIMENTS

Figure 1:
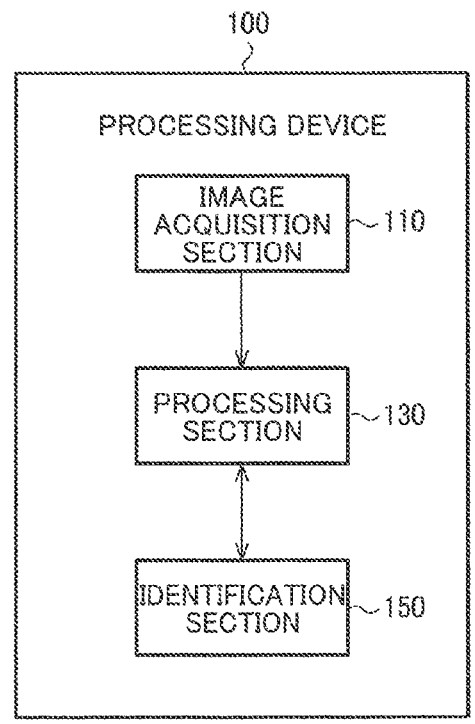
FIG. 1 is a diagram illustrating an example of a system configuration according to an embodiment.

According to one embodiment of the invention, there is provided a processing device comprising:

a processor comprising hardware, the processor being configured to implement:

an image acquisition process of acquiring a tissue image obtained by capturing an image of a tissue; and a process of determining a property of the tissue image acquired, and setting a plurality of identification criteria for identifying a state of the tissue as a normal state or an abnormal state, based on the tissue image and the property of the tissue image.

In the processing device, the processor may newly generate a re-generated identification criterion based on the tissue image, when the property of the tissue image is a first property, to set the plurality of identification criteria including an original identification criterion and the re-generated identification criterion.

In the processing device, the processor may determine that the property of the tissue image is the first property and generate the re-generated identification criterion, when the state of the tissue in the tissue image is an unknown abnormal state.

In the processing device, the processor may correct the original identification criterion based on the tissue image to generate a corrected identification criterion to set the plurality of identification criteria including the original identification criterion and the corrected identification criterion, when the property of the tissue image is a second property.

In the processing device, the processor may determine that the property of the tissue image is the second property and generate the corrected identification criterion when the state of the tissue in the tissue image is a known abnormal state.

In the processing device, the processor may newly generate a re-generated identification criterion based on the tissue image when an organ in the tissue image is a first organ, and correct an original identification criterion to generate a corrected identification criterion when the organ in the tissue image is a second organ.

In the processing device, the first organ may be a non-examination target organ, the second organ may be an examination target organ.

In the processing device, the processor may acquire additional information associated with the tissue image, and determining the property of the tissue image based on the additional information acquired.

In the processing device, the processor may acquire, in the image acquisition process, a learning image appended with a true label indicating that the state of the tissue is the normal state or the abnormal state, and a test image not appended with the true label, the processor may determine a property of the learning image, setting the plurality of identification criteria based on the learning image and the property of the learning image, and identify the state of the tissue in the test image to be the normal state or the abnormal state based on the plurality of identification criteria.

In the processing device, the processor may identify the state of the tissue in an identification accuracy calculation image, based on an identification criterion, as the normal state or the abnormal state, and calculate identification accuracy obtained with the identification criterion.

In the processing device, the processor may correct an original identification criterion based on the tissue image to obtain a corrected identification criterion, obtain the identification accuracy obtained with the corrected identification criterion, and set the corrected identification criterion to be one of the plurality of identification criteria, when the identification accuracy obtained with the corrected identification criterion is high to be equal to or higher than given accuracy.

In the processing device, the processor may newly generate a re-generated identification criterion and set the re-generated identification criterion to be one of the plurality of identification criteria, when the identification accuracy obtained with the corrected identification criterion is lower than the given accuracy.

In the processing device, the processor may generate a new tissue image based on the tissue image acquired, and generate the re-generated identification criterion based on the original tissue image and the new tissue image generated.

In the processing device, the processor may generate the re-generated identification criterion by increasing a weight of a feature amount of the tissue image acquired, in a feature amount distribution of an original identification criterion.

In the processing device, the processor may select a feature amount distribution space of the re-generated identification criterion to generate the re-generated identification criterion.

In the processing device, the processor may perform a limiting process for correction of the original identification criterion and generate the corrected identification criterion.

In the processing device, the processor may perform the limiting process and generate the corrected identification criterion, the limiting process being a process of reducing the weight for the feature amount of the tissue image in the feature amount distribution of the original identification criterion or a process of limiting a range of correcting the original identification criterion in the feature amount distribution space of the original identification criterion.

In the processing device, the processor may perform an identification process of identifying the state of the tissue as the normal state or the abnormal state, based on the plurality of identification criteria.

In the processing device, the processor may perform the identification process based on the original identification criterion, in the plurality of identification criteria, to obtain a first identification result and provide a first weight to the first identification result obtained, and perform the identification by using the corrected identification criterion or the re-generated identification criterion, in the plurality of identification criteria, to obtain a second identification result, and provide a second weight, different from the first weight, to the second identification result.

In the processing device, the processor may obtain a presenting identification result to be presented to a user, based on the first identification result provided with the first weight and the second identification result provided with second weight.

In the processing device, the processor may perform a process of determining a type of an organ in the tissue image or a process or acquiring patient information, and weight an identification result based on the type of the organ determined or the patient information acquired.

In the processing device, the processor may perform the identification process on a first tissue image in a plurality of tissue images obtained by capturing images of the tissue in time series, to obtain a first identification result, perform the identification process on a second tissue image in the plurality of tissue images to obtain a second identification result, the second tissue image being captured at an image capturing timing subsequent to an image capturing timing for the first tissue image, and weight the second identification result based on the first identification result.

In the processing device, the processor may perform a process of transmitting the identification criterions set and the property of the tissue image determined to an external information processing device.

According to another embodiment of the invention, there is provided a processing method comprising:

acquiring a tissue image obtained by capturing an image of a tissue; and determining a property of the tissue image acquired, and setting a plurality of identification criteria for identifying a state of the tissue as a normal state or an abnormal state, based on the tissue image and the property of the tissue image.

According to another embodiment of the invention, there is provided a computer-readable storage device with an executable program stored thereon, wherein the program instructs a microprocessor to perform the following steps of;

acquiring a tissue image obtained by capturing an image of a tissue; and determining a property of the tissue image acquired, and setting a plurality of identification criteria for identifying a state of the tissue as a normal state or an abnormal state, based on the tissue image and the property of the tissue image.

The present embodiment will be described below. Note that the following exemplary embodiments do not in any way limit the scope of the invention laid out in the claims. Note also that not all of the elements described below in connection with the exemplary embodiments should be taken as essential elements of the invention.

1. Overview

In medical sites, a tissue may be identified to be in a normal state or an abnormal state by using a tissue image. In such a case, a rare case is preferably identifiable. Unfortunately, with an identification criterion generated in advance, the rare cases fail to be correctly identified in many cases. In view of this, a method of updating an identification criterion prepared in advance through incremental learning using images actually acquired in a medical site to increase identifiable cases has been under study.

When the original identification criterion is corrected through the incremental learning using all the tissue images acquired, the identification criterion might be largely changed, resulting in a failure to identify cases that have been correctly identifiable. Thus, in the invention disclosed in JP-A-2009-37565 described above, incremental learning data is selected to be used in the incremental learning. Specifically, a feature amount is extracted from incremental learning data, and then only incremental learning data involving an extracted feature amount a distance of which from the original identification criterion is shorter than a given distance in a feature amount distribution space is selected. The incremental learning data thus selected is used for correcting the identification criterion, and incremental learning data not selected is not used in the incremental learning. Thus, in the invention in JP-A-2009-37565, an original identification criterion is updated only with incremental learning data ensuring fine adjustment of the identification criterion. This ensures cases that have been correctly identifiable with the original identification criterion to be correctly identifiable with the corrected identification criterion.

The invention disclosed in JP-A-2009-37565 described above only achieves the fine adjustment of the original identification criterion. In many cases, the resultant identification criterion results in a failure to identify rare cases completely different from cases that have been identifiable. It is a matter of course that not only the cases that have been identifiable but also the rare cases are preferably identifiable.

Thus, a processing device and the like according to the present embodiment improve identification accuracy for a state of a tissue that has not been correctly identifiable with an original identification criterion, without compromising identification accuracy for a state of a tissue that has been correctly identifiable with the original identification criteria. Specifically, in the present embodiment, a method for updating an identification criterion is changed in accordance with a property of a tissue image additionally acquired. For example, the identification criterion may be updated in accordance with whether or not a case indicated by a tissue image is an unknown case. In this configuration, a re-generated identification criterion is generated when the case is an unknown case, and a corrected identification criterion is generated by correcting the original identification criterion when the case is a known case. Then, a plurality of identification criteria including the original identification criterion and at least one of the re-generated identification criterion and the corrected identification criterion are set. The property of a tissue image is not limited to whether or not the case indicated by the tissue image is an unknown case, and may be a type of an organ in a tissue image as described later.

2. System Configuration Example

FIG. 1 illustrates a system configuration example of a processing device according to the present embodiment.

A processing device (image processing device) 100 includes an image acquisition section 110, a processing section 130, and an identification section 150. The image acquisition section 110 is connected to the processing section 130 and the processing section 130 is connected to the identification section 150. Note that the processing device 100 is not limited to the configuration illustrated in FIG. 1, and may be modified in various ways with some of the components omitted or other components added.

Next, processes performed by the sections are described.

The image acquisition section 110 acquires a tissue image obtained by capturing an image of a tissue. For example, the image acquisition section 110 may be an unillustrated image capturing section, or may be an unillustrated communication section that receives data on the tissue image from an external image capturing section through a network. The tissue image is a color image with pixel positions having pixel levels (pixel values) for red (R), green (G), and blue (B) wavelength components for example. For example, the tissue image may be an intraluminal image obtained by capturing an image in a lumen of a subject with an endoscope or the like.

The processing section 130 determines the property of the tissue image acquired, and sets a plurality of identification criteria for identifying the state of a tissue as a normal state or an abnormal state, based on the tissue image and the property of the tissue image. Operations performed by the processing section 130 are described in detail later.

The identification section 150 performs an identification process for identifying the state of the tissue as the normal state or the abnormal state, based on the plurality of identification criteria. Thus, a plurality of identification results can be obtained, and the other like effect can be achieved. Functions of the processing section 130 and the identification section 150 can be implemented with various processors (central processing unit (CPU) or the like), hardware such as an application specific integrated circuit (ASIC) (such as a gate array), a program, or the like.

3. Process Details

Next, an operation performed by the processing device 100 to generate an identification criterion by using a tissue image captured with an endoscope is described in detail.

The identification criterion is prepared and stored in advance in an unillustrated storage section of the processing device 100. This identification criterion has been generated by machine learning by using a learning image prepared in advance.

The learning image is an image obtained by appending a true label to a tissue image. In this example, the true label added is one of a "normal state" label indicating that the state of a tissue is normal, and an "abnormal state" label indicating that the state of the tissue is abnormal.

Figure 2:
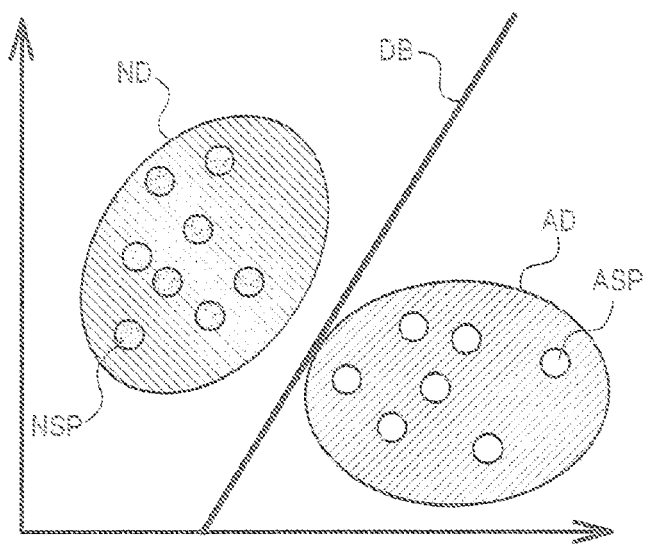
FIG. 2 is a diagram illustrating a normal distribution, an abnormal distribution, and an identification boundary.

For example, the identification criterion is an identification boundary DB as illustrated in FIG. 2. In the example illustrated in FIG. 2, sample data (such as NSP and ASP) is generated with each learning image converted into a feature amount vector, and each sample data is plotted on a feature amount distribution space corresponding to the feature amount vector of the learning image. A distribution of sample data appended with the "normal state" label as the true label is obtained as a normal distribution ND. A distribution of sample data appended with the "abnormal state" label as the true label is obtained as an abnormal distribution AD. Furthermore, the identification boundary DB for identifying the state of a tissue in a tissue image as the normal state or the abnormal state is obtained as the identification criterion. The identification criterion may be generated by the processing device 100, or may be generated by a device or the like other than the processing device 100 and acquired by the processing device 100. Data obtained by converting the learning image into the feature amount vector is hereinafter referred to as the sample data.

For example, when sample data pieces of tissue images, in tissue images acquired in medical sites, indicating the normal state are mostly plotted within the current normal distribution ND as in the case of NSP illustrated in FIG. 2, the current identification criterion can obtain correct identification, and thus does not need to be updated. Similarly, also when sample data pieces of tissue images, in tissue images acquired in medical sites, indicating the abnormal state are mostly plotted within the current abnormal distribution AD, as in the case of ASP illustrated in FIG. 2, the current identification criterion does not need to be updated.

Figure 3:
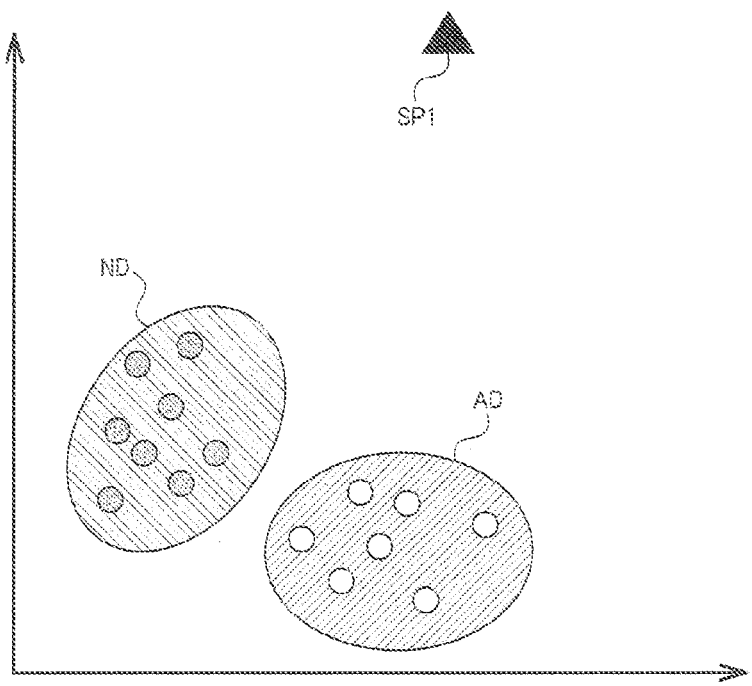
FIG. 3 is a diagram illustrating an unknown abnormal state.
Figure 4:
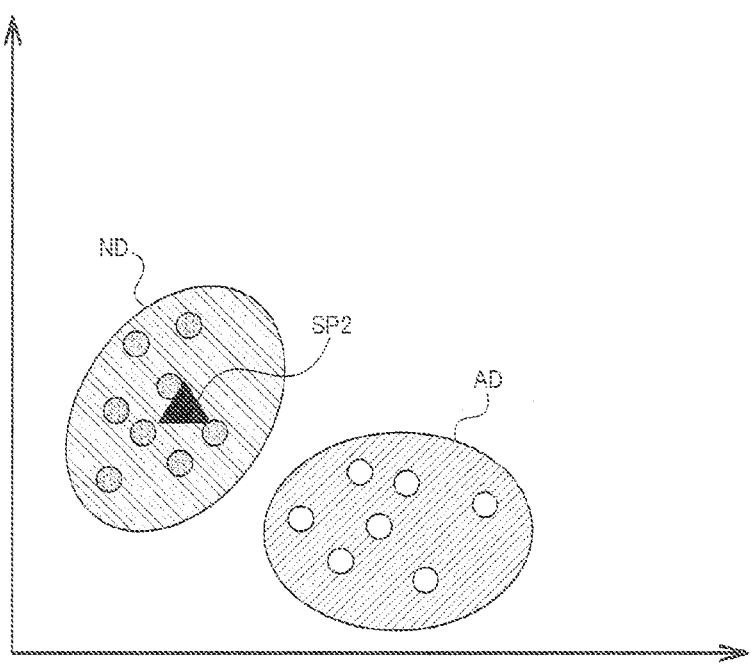
FIG. 4 is another diagram illustrating an unknown abnormal state.

However, in actual cases, as illustrated in FIG. 3, sample data SP1 that is not plotted on neither of the current normal distribution ND nor the current abnormal distribution AD might be acquired. Furthermore, as illustrated in FIG. 4, sample data SP2 plotted on the normal distribution ND might be acquired even when the tissue image includes a tissue in an abnormal state. Conversely, sample data plotted on the abnormal distribution AD might be acquired even a tissue image includes a tissue in the normal state. The identification criterion (original identification criterion) that has been stored in the processing device 100 results in erroneous identification of the state of the tissue indicated by such sample data pieces. Thus, the identification criterion needs to be updated in such cases.

Figure 5:
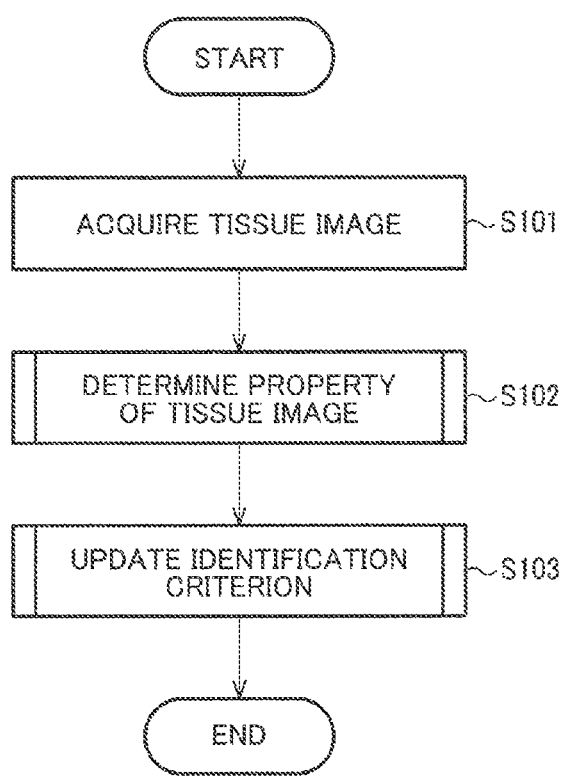
FIG. 5 is a flowchart illustrating a flow of a process according to the embodiment.

Thus, in the present embodiment, a process illustrated in a flowchart in FIG. 5 is performed. More specifically, the image acquisition section 110 acquires a tissue image (S101). The processing section 130 determines the property of the tissue image thus acquired (S102). Then, the processing section 130 determines a method of updating the identification criterion, based on the property of the tissue image, and updates the identification criterion (S103).

More specifically, when the identification criterion is updated by using the tissue image correctly identifiable with the original identification criterion as illustrated in FIG. 2, the corrected identification criterion is generated by correcting the identification criterion. In this case, the identification accuracy can be improved for a tissue image similar to the tissue image correctly identifiable with the original identification criterion. For example, the tissue image, similar to the tissue image correctly identifiable with the original identification criterion, includes a tissue image corresponding to sample data plotted on the feature amount distribution space to be within a given distance from the sample data corresponding to the tissue image correctly identifiable with the original identification criterion. Note that the original identification criterion is not deleted but is used together with the corrected identification criterion.

When the identification criterion is updated by using the tissue image that is likely to be incorrectly identified with the original identification criterion as illustrated in FIG. 3 or FIG. 4, a re-generated identification criterion is newly generated. The tissue image that is likely to be incorrectly identified with the original identification criterion can be correctly identified with the re-generated identification criterion. Also in this case, the original identification criterion is not deleted and is used together with the re-generated identification criterion.

With the configuration described above, the identification accuracy can be improved for the state of the tissue that has not been correctly identifiable with the original identification criterion, without compromising the identification accuracy for the state of the tissue that has been correctly identifiable with the original identification criterion.

The process described above is summarized as follows. For a tissue image with a first property, the processing section 130 newly generates the re-generated identification criterion based on the tissue image, to set a plurality of identification criteria including the original identification criterion and the re-generated identification criterion.

The re-generated identification criterion is a newly generated identification criterion different from the original identification criterion. The re-generated identification criterion may be obtained as a linear discriminant function in a desired feature amount space, or may be generated with a Support Vector Machine (SVM) or the like. The SVM is one of pattern recognition models using supervised learning. When the SVM is employed, the maximum-margin hyperplane is obtained as a pattern identifier (identification criterion). The maximum-margin hyperplane divides learning data pieces, plotted on a given feature amount distribution space, into two classes with the distance between the hyperplane and the nearest point in each class maximized For example, the original identification criterion includes an identification criterion stored in the storage section or the like of the processing device 100 in advance, an identification criterion acquired from an external device, an identification criterion generated from a learning image stored in advance in the storage section and the like of the processing device 100, and the like.

Thus, for example, the state of the tissue that has not been correctly identifiable with the original identification criterion can be identified with the re-generated identification criterion, the state of the tissue that has been correctly identifiable with the original identification criterion can be identified with the original identification criterion, and the other like effect can be achieved.

More specifically, the processing section 130 determines that the tissue image including a tissue with an unknown abnormal state has the first property, and generates the re-generated identification criterion for such an image. For example, the first property indicates that the tissue in the tissue image is in an unknown abnormal state.

The unknown abnormal state is an abnormal state of a tissue, in a tissue image, corresponding to sample data not plotted within a currently known range of abnormal distributions. For example, when the true label appended to the sample data SP1 illustrated in FIG. 3 described above indicates the abnormal state, the tissue indicated by the sample data SP1 is in the unknown abnormal state.

Thus, the re-generated identification criterion with which the unknown abnormal state can be identified can be generated and the other like effect can be achieved.

When a tissue image has a second property, the processing section 130 corrects the original identification criterion based on the tissue image to generate the corrected identification criterion, and thus sets a plurality of identification criteria including the original identification criterion and the corrected identification criterion.

The corrected identification criterion is an identification criterion that is obtained by correcting the original identification criterion and is different from the original identification criterion. For example, the corrected identification criterion is obtained by sequential learning such as Passive-Aggressive. The Passive-Aggressive is one method of the sequential learning, in which the identification criterion is updated each time a single learning data is provided.

Thus, for example, the identification accuracy can be improved through fine adjustment of the original identification criterion and the other like effect can be achieved.

Specifically, the processing section 130 determines that a tissue image including a tissue in a known abnormal state has the second property, and generates the corrected identification criterion for such an image. For example, the second property indicates that the tissue in the tissue image is in a known abnormal state.

The known abnormal state is an abnormal state of a tissue, in a tissue image, corresponding to sample data plotted within a currently known range of abnormal distributions. For example, a tissue corresponding to the sample data ASP illustrated in FIG. 2 is in the known abnormal state.

With this configuration, identification accuracy can be improved for known abnormal states, and the other like effect can be achieved.

In the case described above, the abnormal state label is appended to a new tissue image acquired, the first property corresponds to an unknown abnormal state, and the second property corresponds to a known abnormal state. However, this should not be construed in a limiting sense. For example, when a tissue in the new tissue image acquired is in a normal state, the first property may correspond to an unknown normal state and the second property may correspond to a known normal state, for example.

The processing section 130 acquires additional information associated with a tissue image, and determines the property of the tissue image based on the additional information acquired.

For example, the additional information includes the diagnosis of a case (state) found in a tissue image described later and a true label, indicating the state of a tissue (the abnormal state or the normal state), appended to the tissue image by a physician.

Thus, for example, when the diagnosis of a case found in the tissue image is acquired as the additional information, the state (the unknown abnormal state, the known abnormal state, the unknown normal state, and the known normal state) indicated by the property of the tissue image can be determined and the other like effect can be achieved.

Next, a flow of a specific process for determining the property of a tissue image is described with reference to flowcharts in FIG. 6 to FIG. 10.

Figure 6:
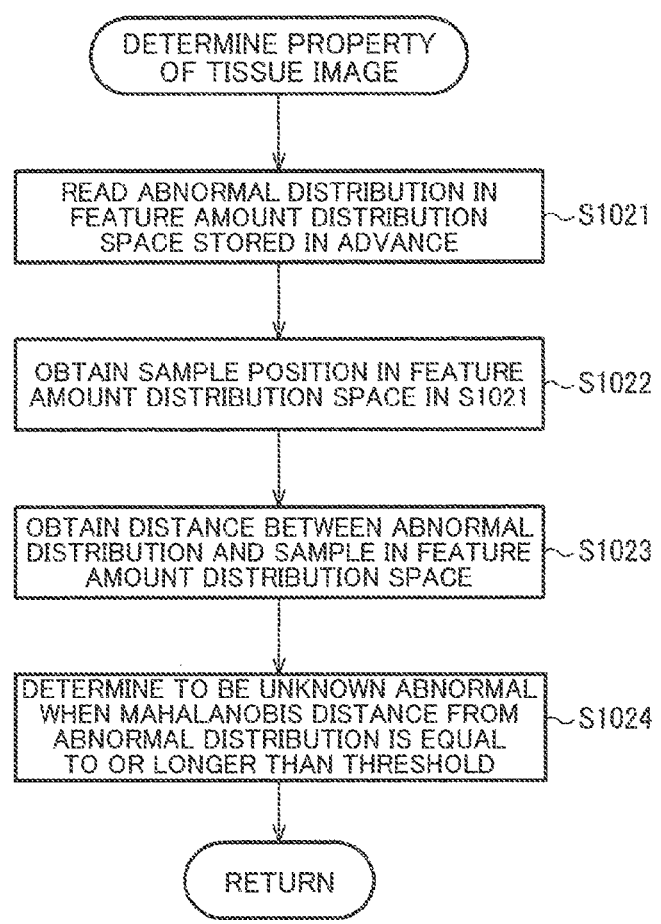
FIG. 6 is a flowchart illustrating a flow of a tissue image property determination process.
Figure 7:
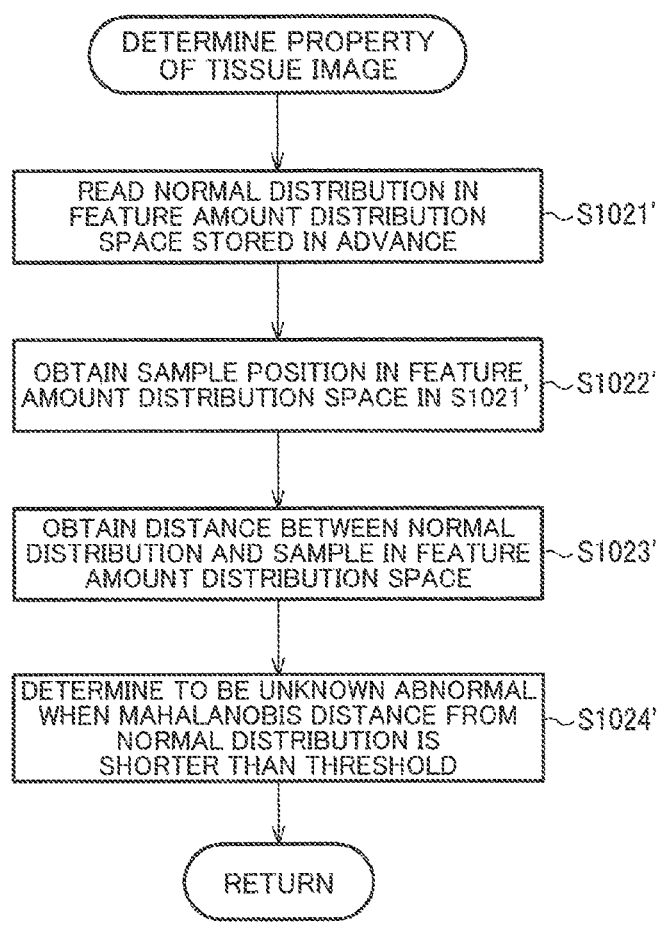
FIG. 7 is another flowchart illustrating a flow of a tissue image property determination process.

Examples in FIG. 6 and FIG. 7 correspond to cases where the tissue image newly acquired in step S101 is appended with the abnormal state label serving as the additional information.

First of all, in the example illustrated in FIG. 6, the property of an acquired sample (the property of a tissue image) is determined to be an unknown abnormal state when the sample, appended with the abnormal state label, is not plotted within the range of the current abnormal distribution. Specifically, the processing section 130 reads an abnormal distribution in a feature amount distribution space stored in the storage section in advance (S1021). Next, the processing section 130 plots a sample, corresponding to the tissue image acquired in step S101, on the feature amount distribution space thus read, and obtains the sample position (S1022). Then, the processing section 130 obtains a Mahalanobis distance between the abnormal distribution and the sample in the feature amount distribution space (S1023). When the Mahalanobis distance thus obtained is equal to or longer than a given threshold, the tissue is determined to be in the unknown abnormal state (S1024).

In the example illustrated in FIG. 7, the property of an acquired sample (property of a tissue image) is determined to be an unknown abnormal state, when the sample appended with the abnormal state label is plotted within a range of a current normal distribution. Specifically, the processing section 130 reads a normal distribution in the feature amount distribution space stored in the storage section in advance (S1021'). Next, the processing section 130 plots a sample, corresponding to the tissue image acquired in step S101, on the feature amount distribution space thus read, and obtains the sample position (S1022'). Then, the processing section 130 obtains a Mahalanobis distance between the normal distribution and the sample in the feature amount distribution space (S1023'). When the Mahalanobis distance thus obtained is shorter than a given threshold, the tissue is determined to be in the unknown abnormal state (S1024').

Only one of the processes illustrated in the flowcharts in FIG. 6 and FIG. 7 may be performed. Still, the processes are preferably both performed.

Figure 8:
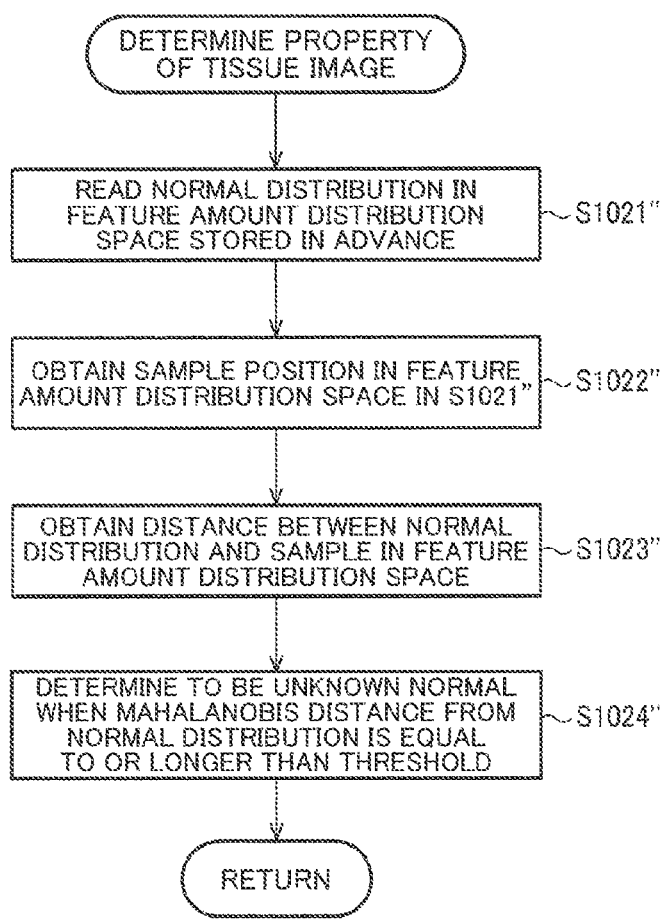
FIG. 8 is another flowchart illustrating a flow of a tissue image property determination process.
Figure 9:
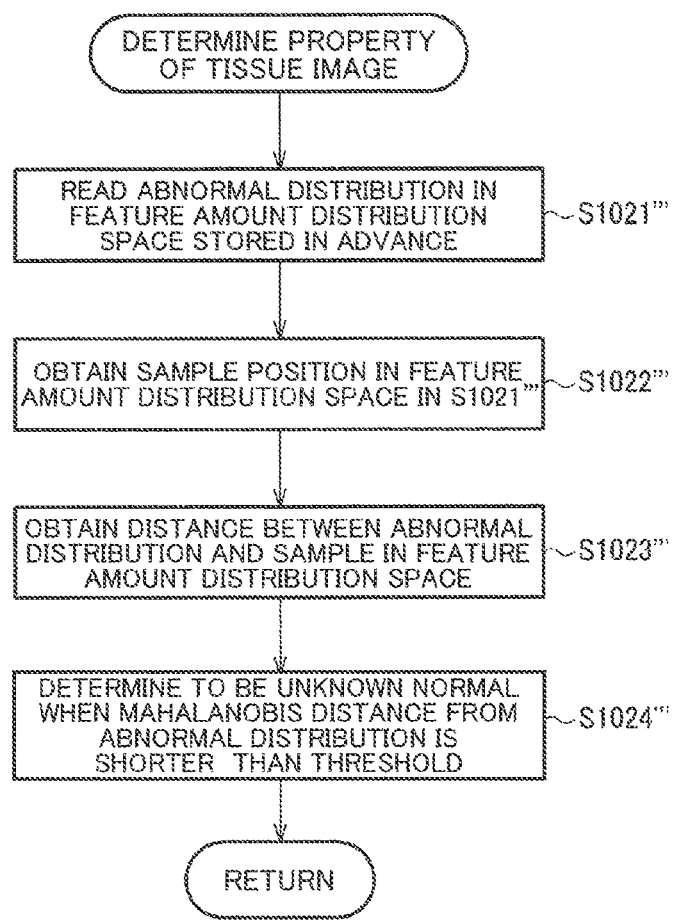
FIG. 9 is another flowchart illustrating a flow of a tissue image property determination process.

Examples in FIG. 8 and FIG. 9 correspond to cases where the normal state label is appended to the additional information to a tissue image newly acquired in step S101.

In the example illustrated in FIG. 8, the property of an acquired sample (property of a tissue image) is determined to be an unknown normal state, when the sample is appended with the normal state label but is not plotted within a range of a current normal distribution. Specifically, the processing section 130 reads the normal distribution in the feature amount distribution space stored in the storage section in advance (S1021"). Next, the processing section 130 plots a sample, corresponding to the tissue image acquired in step S101, on the feature amount distribution space thus read, and obtains the sample position (S1022"). Then, the processing section 130 obtains a Mahalanobis distance between the normal distribution and the sample in the feature amount distribution space (S1023"). When the Mahalanobis distance thus obtained is equal to or longer than a given threshold, the tissue is determined to be in the unknown normal state (S1024").

In the example illustrated in FIG. 9, the property of an acquired sample (property of a tissue image) is determined to be an unknown normal state, when the sample is appended with the normal state label but is plotted within the range of the current abnormal distribution. Specifically, the processing section 130 reads the abnormal distribution in the feature amount distribution space stored in the storage section in advance (S1021'''). Next, the processing section 130 plots a sample, corresponding to the tissue image acquired in step S101, on the feature amount distribution space thus read, and obtains the sample position (S1022'''). Then, the processing section 130 obtains a Mahalanobis distance between the abnormal distribution and the sample in the feature amount distribution space (S1023'''). When the Mahalanobis distance thus obtained is shorter than a given threshold, the tissue is determined to be in the unknown normal state (S1024''').

Also in these cases, only one of the processes illustrated in the flowcharts in FIG. 8 and FIG. 9 may be performed. Still, the processes are preferably both performed. An example in FIG. 10 corresponds to a case where a diagnosis, as a result of diagnosis by a physician on a subject, is added as the additional information to the tissue image newly acquired in step S101.

Figure 10:
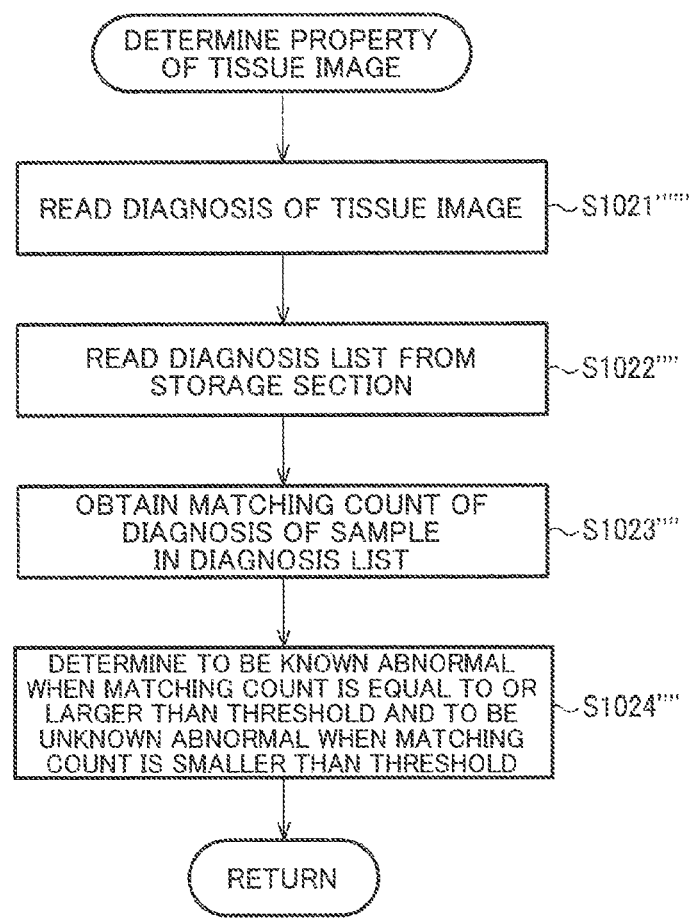
FIG. 10 is another flowchart illustrating a flow of a tissue image property determination process.

In the example illustrated in FIG. 10, the state of a tissue in a tissue image appended with diagnosis that has been sufficiently learned is determined as a known abnormal state (or a known normal state), and the state of a tissue in a tissue image appended diagnosis not sufficiently learned diagnosis is determined as an unknown abnormal state (or an unknown normal state).

Figure 11:
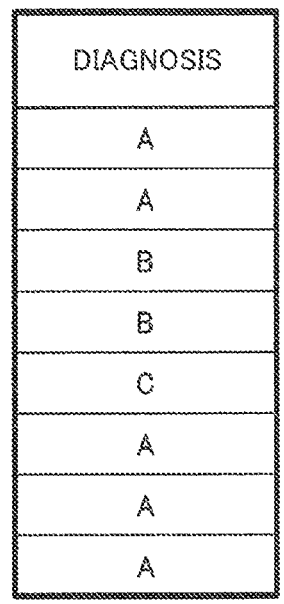
FIG. 11 is a diagram illustrating a diagnosis list.

Specifically, the processing section 130 reads a diagnosis appended to the newly acquired tissue image (S1021''''), and reads the diagnosis list from the storage section (S1022''''). The diagnosis list is a list as illustrated in FIG. 11. In the list, diagnosis provided to tissue images that have been used in the learning are registered. Next, the processing section 130 obtains the matching count of the diagnosis of the sample, corresponding to the acquired tissue image, with the diagnoses registered in the diagnosis list (S1023''''). The processing section 130 determines that the state of the tissue is a known abnormal state (or a known normal state) when the matching count thus obtained is equal to or larger than a given threshold, and determines that the state of the tissue is an unknown abnormal state (or an unknown normal state), when the matching count thus obtained is smaller than the given threshold (S1024''''). For example, in an example illustrated in FIG. 11, when the diagnosis of the sample is A, the matching count is 5. In this condition, when the given threshold is 2, the state of the tissue is determined to be a known abnormal state (or a known normal state). For example, when the diagnosis of the sample is C, the matching count is 1, and thus the state of the tissue is determined to be an unknown abnormal state (or an unknown normal state).

Next, a flow of a process of updating the identification criterion in step S103 is described in detail with reference to flowcharts in FIG. 12 to FIG. 15.

Figure 12:
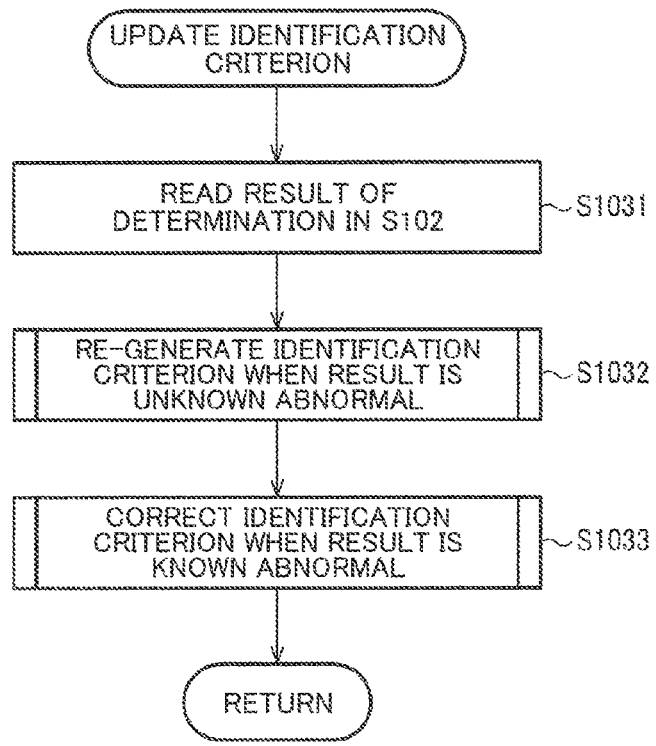
FIG. 12 is a flowchart illustrating a flow of an identification criterion update process.

First of all, as illustrated in the flowchart in FIG. 12, the processing section 130 reads the result of the determination in step S102 (S1031). The result indicates that the state of the tissue, in the newly acquired tissue image, is an unknown abnormal state or a known abnormal state (an unknown normal state or a known normal state). As described above, when the processing section 130 determines that the tissue is in an unknown abnormal state (unknown normal state), the re-generated identification criterion is generated (S1032). When the processing section 130 determines that the tissue is in a known abnormal state (known normal state), the corrected identification criterion is generated (S1033).

Next, a modification of the process in step S1032 is described. A tissue image including a tissue in an unknown abnormal state or an unknown normal state is difficult to acquire. However, an identification criterion obtaining high identification accuracy requires to be generated with a predetermined number of learning images (tissue images) or more.

Figure 13:
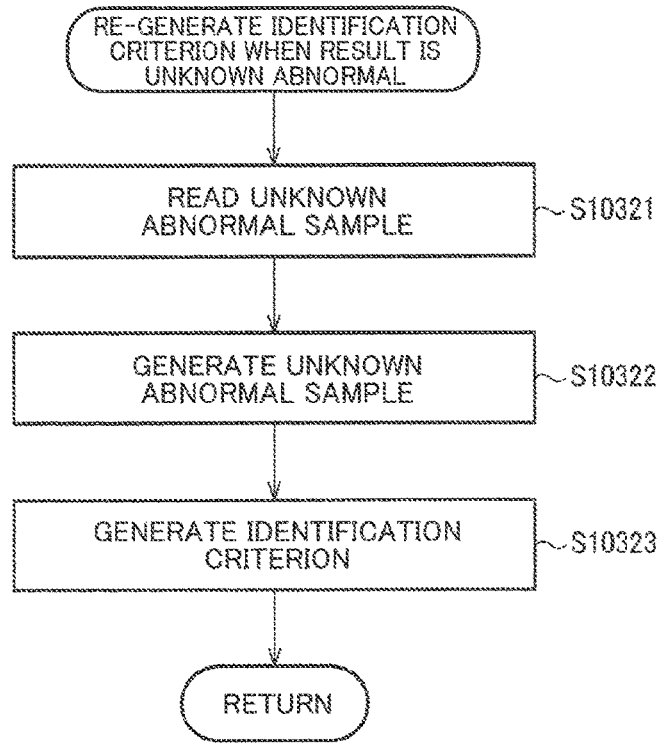
FIG. 13 is a flowchart illustrating a flow of a re-generated identification criterion generation process.

Thus, as illustrated in the flowchart in FIG. 13, the processing section 130 reads a sample in an unknown abnormal state (S10321), and then generates a new sample in an unknown abnormal state based on the sample in the unknown abnormal state thus read (S10322). Specifically, the new sample in the unknown abnormal state may be generated based on a tissue image as a result of rotating the read tissue image by an appropriate angle and in an appropriate direction. Then, the processing section 130 generates the re-generated identification criterion based on the sample in the unknown abnormal state read in step S10321 and the sample in the unknown abnormal state newly generated in step S10322 (S10323).

In other words, the processing section 130 generates a new tissue image based on an acquired tissue image, and generates the re-generated identification criterion based on the original tissue image and the newly generated tissue image.

Thus, the identification accuracy obtained with the re-generated identification criterion can be improved and the other like effect can be achieved.

As described above, the tissue image including a tissue in an unknown abnormal state or an unknown normal state is difficult to acquire, and thus the number of such images is small. The number of tissue images including tissues in known abnormal states or known normal states is large. Thus, the identification criterion is generated with the identification accuracy prioritized on a tissue image including a tissue in a known abnormal state or a known normal state.

Figure 14:
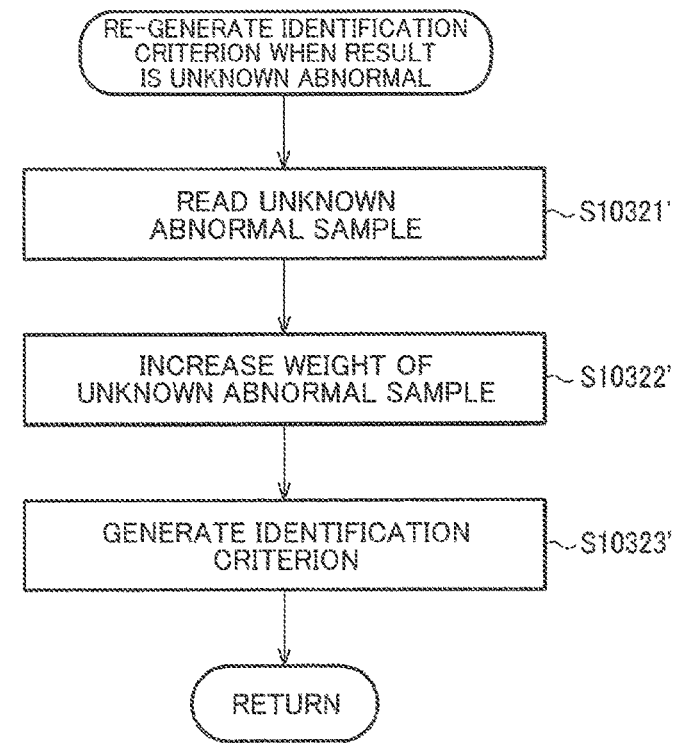
FIG. 14 is another flowchart illustrating a flow of a re-generated identification criterion generation process.

In view of this, as illustrated in the flowchart in FIG. 14, the processing section 130 reads a sample in an unknown abnormal state (S10321'), and increases a weight of the sample in the unknown abnormal state thus read, in a feature amount distribution of the original identification criterion (S10322'). Then, the processing section 130 generates the re-generated identification criterion based on the sample in the unknown abnormal state the weight of which has been increased (S10323').

Specifically, the processing section 130 generates the re-generated identification criterion by increasing the weight of the feature amount of the acquired tissue image, in the feature amount distribution of the original identification criterion.

Thus, the identification accuracy for the state of the tissue in the newly acquired tissue image can be improved and the other like effect can be achieved. Specifically, the re-generated identification criterion obtaining high identification accuracy for a tissue image including a tissue in an unknown abnormal state or an unknown normal state and the like can be generated and the other like effect can be achieved.

In the present embodiment, as described above, the sample data that is a feature amount vector is generated from a tissue image, and the identification criterion is generated based on the sample data thus generated. In this configuration, the identification accuracy might be higher in a case where only a part of the feature amounts of the tissue image is used to generate the feature amount vector to generate the identification criterion, than in a case where all of the feature amounts of the tissue image are used to generate the feature amount vector. For example, for a tissue image with a distinctive color, it might be better to generate the feature amount vector by using feature amounts representing the color only.

Figure 15:
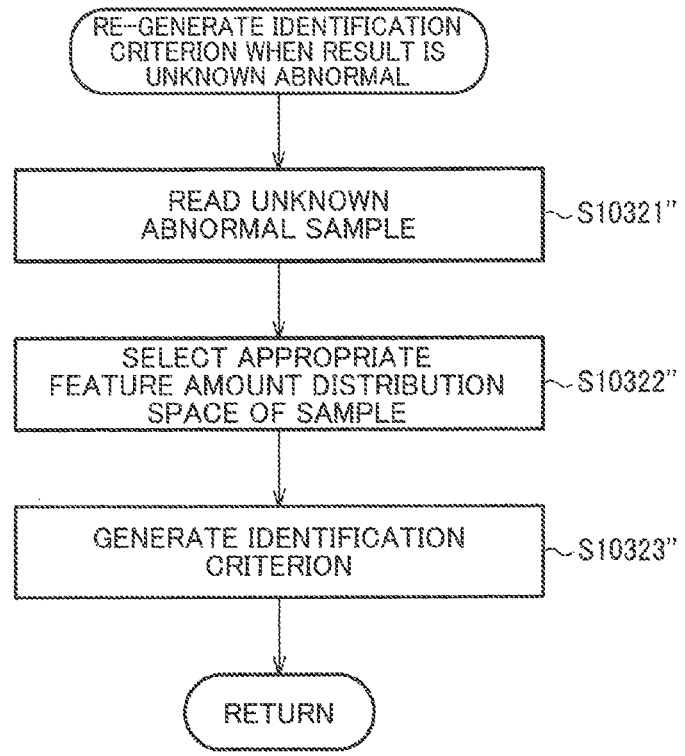
FIG. 15 is another flowchart illustrating a flow of a re-generated identification criterion generation process.

Thus, as illustrated in the flowchart in FIG. 15, the processing section 130 reads a sample in an unknown abnormal state (S10321"), and selects the feature amount distribution space of the sample in the unknown abnormal state thus read (S10322"). Then, the processing section 130 generates the re-generated identification criterion based on the sample in the unknown abnormal state in the selected feature amount distribution space (S10323").

Thus, the processing section 130 selects the feature amount distribution space of the re-generated identification criterion to generate the re-generated identification criterion.

For example, the feature amount distribution space held in advance can be regarded as an m-dimensional original feature amount distribution space selected from n-dimensional original feature amounts of the tissue image. The original feature amount distribution space is a feature amount distribution space optimum for setting an identification criterion for the original normal distribution and the original abnormal distribution, but may not be suitable for generating an identification criterion for an unknown abnormality.

Thus, an m'-dimensional original feature amount distribution space optimum for an identification criterion for identifying an unknown abnormal state, is selected from the n-dimensional feature amounts of the tissue image. A series of processes is described below.

First of all, n-dimensional feature amounts $[x_{11}, x_{12}, \ldots, x_{1n}], [x_{21}, x_{22}, \ldots, x_{2n}], \ldots [x_{p1}, x_{p2}, \ldots, x_{p2}]$ of p samples in an unknown abnormal state and q n-dimensional feature amounts $[y_{11}, y_{12}, \ldots, y_{1n}], [y_{21}, y_{22}, \ldots, y_{2n}], \ldots, [y_{q1}, y_{q2}, \ldots, y_{qn}]$ of a normal distribution held in advance are read. Next, principal component analysis that is a known technique is performed to obtain coefficients $[\alpha_{11}, \alpha_{12}, \ldots, \alpha_{1n}], [\alpha_{21}, \alpha_{22}, \ldots, \alpha_{2n}], \ldots [\alpha_{t1}, \alpha_{t2}, \ldots, \alpha_{tn}]$ with t highest contributions. Then, the m'-dimensional original feature amount distribution space, obtained by multiplying any m' highest coefficients, is selected.

Figure 16:
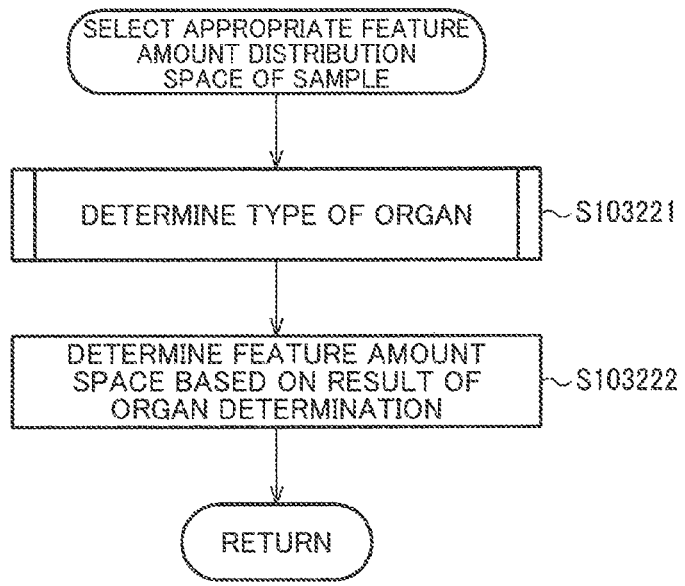
FIG. 16 is a flowchart illustrating a flow of a feature amount distribution space determination process.
Figures 17, 18:
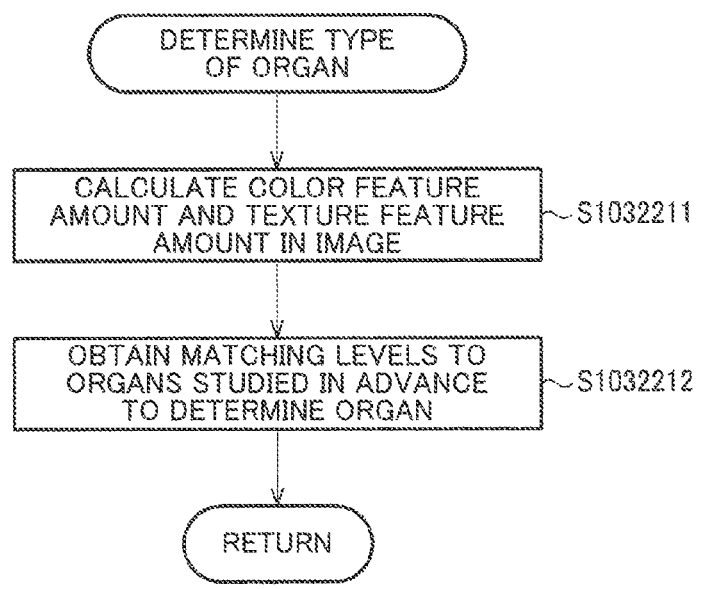
FIG. 17 is a flowchart illustrating an organ type determination process.
FIG. 18 is a diagram illustrating association between types of organs and feature amounts used.

Furthermore, a process of determining a feature amount distribution space from an organ determination result, instead performing the principal component analysis, is described. FIG. 16 is a flowchart illustrating this process. The processing section 130 determines the type of the organ in a tissue image (S103221). FIG. 17 is a flowchart illustrating the process in step S103221. In this process, the processing section 130 calculates a color feature amount and a texture feature amount in the tissue image (S1032211), and a matching level relative to each organ that has been studied in advance to determine the type of the organ (S1032212).

The color feature is based on a color ratio, and is obtained as an average value of G/R and B/G. The texture feature amount is obtained as a Local Binary Pattern (hereinafter, referred to as LBP). The LBP, serving as a feature amount, is a 256 ($2^8$)-dimensional original histogram representing a magnitude relationship among a target pixel and eight peripheral pixels. A value obtained by summing values of the histogram representing the magnitude relationship among each pixel and the eight peripheral pixels in a labeling area is used.

Then, the processing section 130 selects the feature amount distribution space based on a result of determining the type of the organ (S103222). For example, as illustrated in a table in FIG. 18, a feature amount distribution space including the color feature amount and the texture feature amount is selected when the organ in the tissue image is the stomach or the small intestine. A feature amount distribution space including a shape feature amount is selected when the organ in the tissue image is the large intestine. Roundness, a Feret's diameter, an area, or the like is used as the shape feature amount.

As described above, only a part of the feature amounts of the tissue image is used to generate the feature amount vector to generate the re-generated identification criterion. Thus, the identification accuracy obtained with a new identification criterion can be improved and the other like effect can be obtained with the feature amount distribution space including feature amounts optimum for generating the new identification criterion (re-generated identification criterion) selected.

Next, a modification of the process in step S1033 is described. A corrected identification criterion generated to be largely different from the original identification criterion results in low identification accuracy for the state of the tissue that has been correctly identifiable with the original identification criterion.

Thus, the processing section 130 performs a process for limiting correction of the original identification criterion and generates the corrected identification criterion.

Thus, the identification accuracy for the state of the tissue that has been correctly identifiable with the original identification criterion can be prevented from compromising and the other like effect can be achieved.

Figure 19:
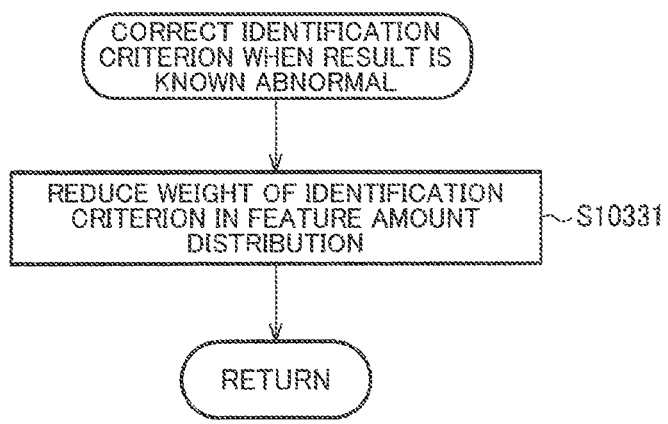
FIG. 19 is a flowchart illustrating a flow of a corrected identification criterion generation process.
Figure 20:
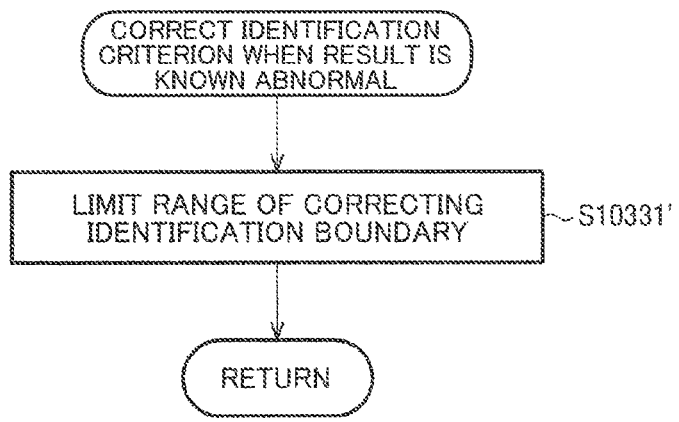
FIG. 20 is another flowchart illustrating a flow of a corrected identification criterion generation process.

Specifically, the processing section 130 performs the limiting process and generates the corrected identification criterion. The limiting process thus performed is a process of reducing the weight of the feature amount of the tissue image in the feature amount distribution of the original identification criterion (S10331 in FIG. 19) or a process of limiting a range of correcting the original identification criterion in the feature amount distribution space of the original identification criterion (S10331' in FIG. 20).

With this process, the difference between the original identification criterion and the corrected identification criterion can be reduced and the other like effect can be achieved.

The process (learning) for generating an identification criterion has been described above in detail. The identification criterion thus generated through the learning is used for identifying the state of a tissue.

Specifically, the image acquisition section 110 acquires a learning image appended with a true label indicating the state (the normal state or the abnormal state) of the tissue and a test image appended with no true label. Then, the processing section 130 determines the property of the learning image thus acquired and sets the plurality of identification criteria based on the learning image and the property of the learning image. Then, the identification section 150 identifies the state of the tissue in the test image as the normal state or the abnormal state, based on the plurality of identification criteria.

The test image is a tissue image appended with no true label, and is a tissue image that is acquired when a physician or the like actually diagnoses a subject for example.

This configuration facilitates determination of the state of a tissue in a great number of test images by the physician or the like.

4. First Modification

Next, a first modification is described. In the first modification, the corrected identification criterion is generated, and then identification accuracy obtained with the corrected identification criterion is calculated in a learning stage (a stage of generating the identification criterion). When the identification accuracy thus calculated is equal to or higher than given accuracy, the corrected identification criterion is set as one of the plurality of identification criteria used in the identification process. On the other hand, when the identification accuracy is lower than the given accuracy, the re-generated identification criterion is generated to be used as one of the plurality of identification criteria used in the identification process. Thus, in the first modification, whether or not the identification accuracy obtained with the corrected identification criterion is determined to be equal to or higher than the given accuracy in advance in the learning stage. If the identification accuracy obtained with the corrected identification criterion is equal to or higher than the given accuracy, the re-generated identification criterion is not generated. The corrected identification criterion involves a smaller processing amount than in a case where the re-generated identification criterion is generated. Thus, this modification can reduce the processing amount. The re-generated identification criterion is generated only when the identification accuracy obtained with the corrected identification criterion is lower than the given accuracy. This ensures the identification accuracy equal to or higher than the given accuracy. This identification accuracy calculation process is different from the identification process on the test image described above.

Figure 21:
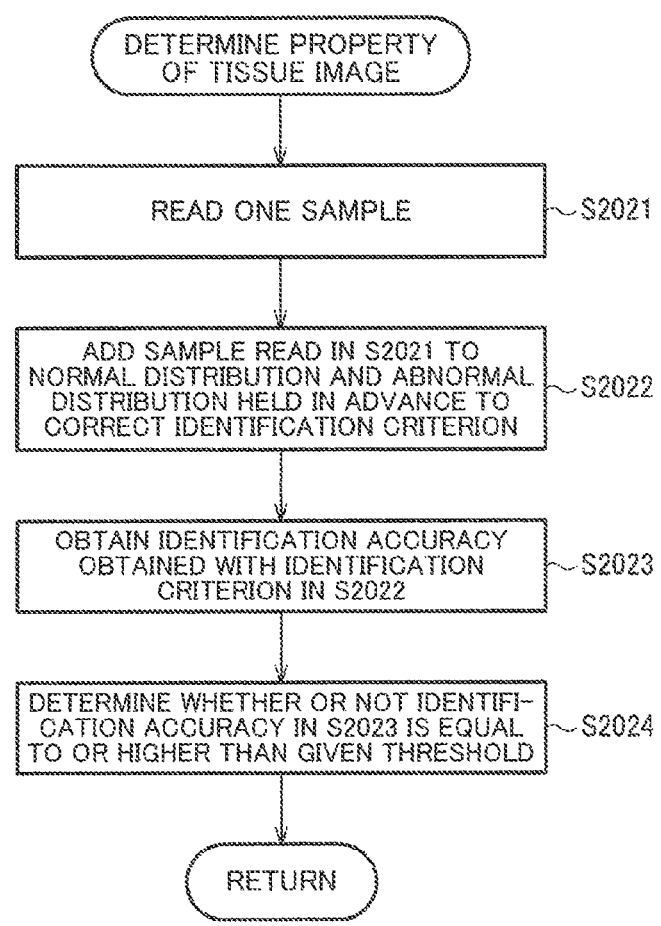
FIG. 21 is a flowchart illustrating a flow of a process according to a first modification.

A flow of the process according to the first modification is basically the same as the flow illustrated in FIG. 5, but is different from the flow in FIG. 5 in the process corresponding to step S102. FIG. 21 is a flowchart illustrating the flow of the process corresponding to step S102.

First of all, the processing section 130 reads one sample (S2021), and generates the corrected identification criterion by adding the sample thus read to the normal distribution and the abnormal distribution obtained in advance (S2022).

Then, the identification section 150 identifies the state of the tissue in an identification accuracy calculation image as the normal state or the abnormal state, based on the identification criterion, and calculates the identification accuracy obtained with the identification criterion.

The identification accuracy calculation image is a tissue image appended with the true label, and is used for calculating the identification accuracy. The test image described above is appended with no true label, and is used in the identification stage. The identification accuracy calculation image is appended with the true label and is used in the learning stage. The test image and the identification accuracy calculation image described above are different from each other in this point. The identification accuracy calculation image is appended with the corrected label so that the identification accuracy can be calculated through comparison between the true label and the identification result. The identification section 150 identifies the state of the tissue in the identification accuracy calculation image as the normal state or the abnormal state by obtaining the identification result, without referring to the true label provided to the identification accuracy calculation image. The identification section 150 refers to the true label only when calculating the identification accuracy based on the identification result.

For example, when the identification accuracy is calculated, the identification result is acquired by actually using the identification criterion to perform the identification process on the identification accuracy calculation image. Then, the identification section 150 compares the identification result with the true label that has been appended to the identification accuracy calculation image in advance, to obtain the matching level (true level) serving as the identification accuracy (S2023).

Thus, whether the re-generated identification criterion is to be generated or the corrected identification criterion is to be generated can be determined and the other like effect can be achieved based on the identification accuracy obtained with the current identification criterion.

More specifically, the processing section 130 corrects the original identification criterion based on the tissue image to obtain the corrected identification criterion (S2022). Then, the identification section 150 obtains the identification accuracy obtained with the corrected identification criterion (S2023). The processing section 130 determines whether or not the identification accuracy obtained with the corrected identification criterion is equal to or higher than the given accuracy (S2024). When the identification accuracy obtained with the corrected identification criterion is high to be equal to or higher than the given accuracy, the corrected identification criterion is set to be one of the plurality of identification criteria.

Thus, the process for generating the re-generated identification criterion can be cancelled and the other like process can be performed when the identification accuracy obtained with the corrected identification criterion is high to be equal to or higher than the given accuracy. Thus, the processing amount can be reduced.

The processing section 130 generates a new re-generated identification criterion when the identification accuracy obtained with the corrected identification criterion is lower than the given accuracy, and sets the re-generated identification criterion to be one of the plurality of identification criteria.

Thus, the identification accuracy can be improved and the other like effect can be obtained with the re-generated identification criterion generated when the identification accuracy obtained with the corrected identification criterion is lower than the given accuracy.

5. Second Modification

Figure 22:
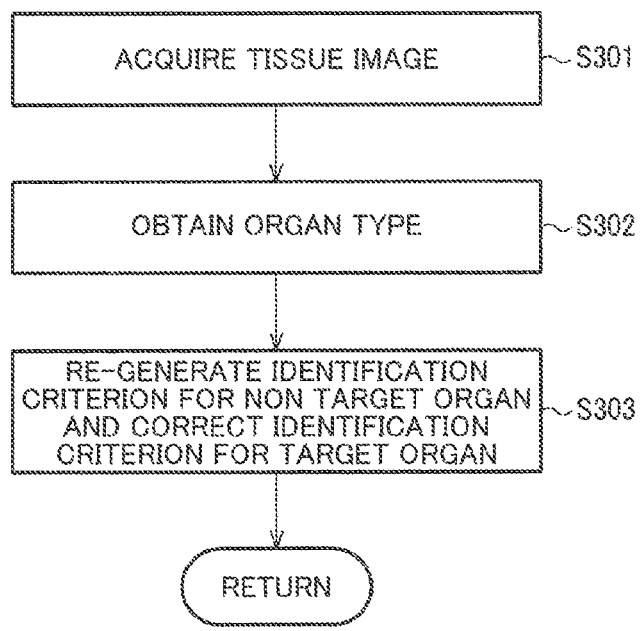
FIG. 22 is a flowchart illustrating a flow of a process according to a second modification.

Next, a second modification is described. In the second modification, whether the re-generated identification criterion is to be generated or the corrected identification criterion is to be generated is determined based on the type of the organ in the tissue image. FIG. 22 is a flowchart illustrating a flow of a process according the second modification.

Figure 23:
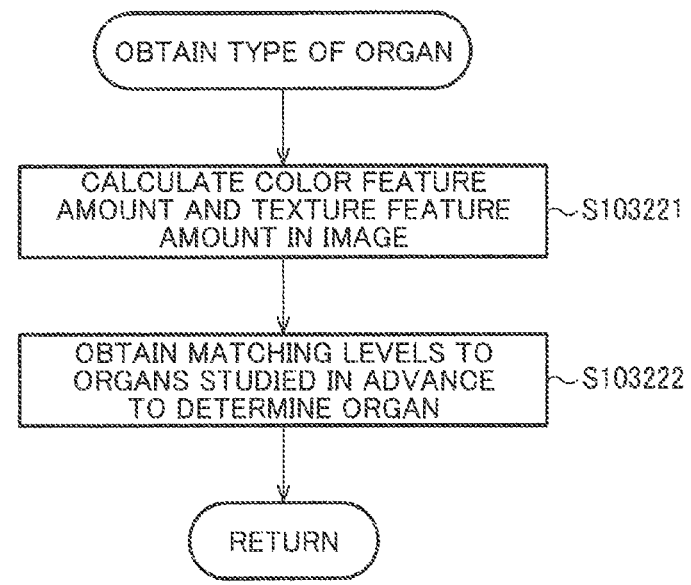
FIG. 23 is a flowchart illustrating a flow of an organ type determination process.

First of all, the image acquisition section 110 acquires a tissue image (S301). Then, the processing section 130 obtains the type of the organ in the tissue image acquired (S302). FIG. 23 is a flowchart illustrating the process in step S302. In this process, the processing section 130 calculates the color feature amount and the texture feature amount in the tissue image (S103221), and obtains the matching level to each organ learned in advance to determine the type of the organ (S103222).

When the organ in the tissue image is a first organ, the processing section 130 generates a new re-generated identification criterion based on the tissue image. When the organ in the tissue image is a second organ, the processing section 130 corrects the original identification criterion based on the tissue image to generate the corrected identification criterion.

Thus, the method of generating the identification criterion can be changed based on the type of the organ in the tissue image and the other like effect can be achieved.

Figures 24, 25:
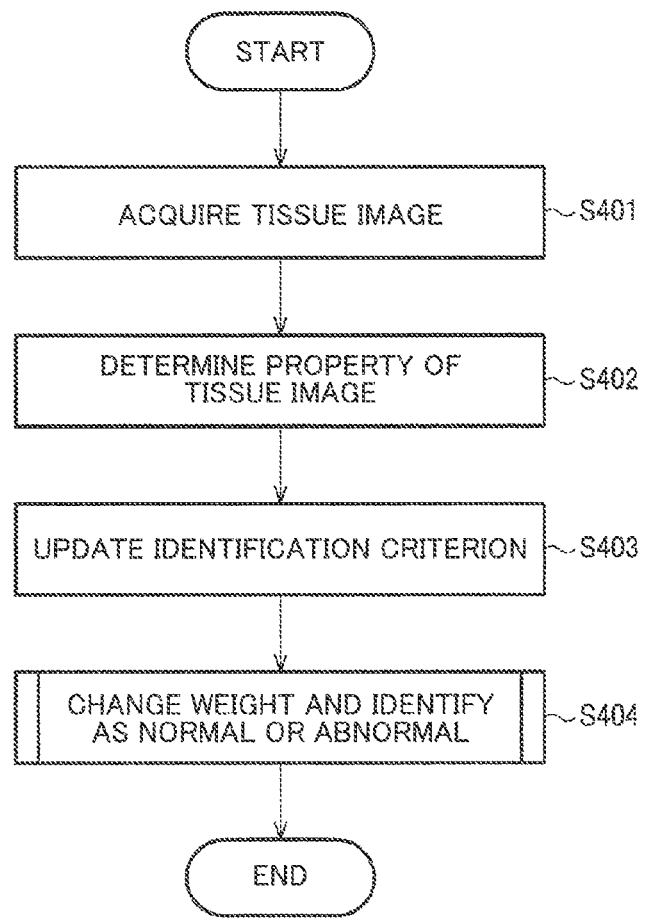
FIG. 24 is a diagram illustrating association between types of organs and identification criterion generation methods.
FIG. 25 is a flowchart illustrating a flow of a process that is a modification of an identification process.

Specifically, the first organ is a non-examination target organ, and the second organ is an examination target organ. Thus, the processing section 130 generates a new re-generated identification criterion based on a tissue image, when the organ in the tissue image is a non-examination target organ, and corrects the original identification criterion based on the tissue image to generate a corrected identification criterion when the organ in the tissue image is an examination target organ (S303). For example, as illustrated in FIG. 24, the re-generated identification criterion is generated when the organ in the tissue image is the stomach or the large intestine, and the corrected identification criterion is generated when the organ in the tissue image is the small intestine.

Thus, when the organ in the tissue image is a non-examination target organ, the state of a tissue that has not been identifiable with the original identification criterion can be identified, when the organ in the tissue image is an examination target organ, the identification accuracy for the state of the tissue that has been identifiable with the original identification criterion can be prevented from compromising, and the other like effect can be obtained.

6. Modification of Identification Process

Next, a modification of the identification process is described. FIG. 25 is a flowchart illustrating a flow of this modification. Steps S401 to S403 are respectively the same as steps S101 to S103 in FIG. 5. The identification section 150 weights each of the identification results obtained with a plurality of identification criteria, and identifies the state of the tissue in the tissue image as a normal state or an abnormal state (S404).

Specifically, the identification section 150 performs an identification process based on the original identification criterion in the plurality of identification criteria to obtain a first identification result, and provides a first weight to the first identification result thus obtained. Next, the identification section 150 performs an identification process by using the corrected identification criterion or the re-generated identification criterion in the plurality of identification criteria to obtain a second identification result, and provides a second weight, different from the first weight, to the second identification result thus obtained.

With this configuration, which one of the plurality of identification results should be prioritized can be presented to the user, and the other like effect can be obtained.

The identification section 150 obtains a presenting identification result to be presented to the user, based on the first identification result provided with the first weight and the second identification result provided with the second weight.

Thus, the identification result that can be easily understood can be presented to the user, and the other like effect can be achieved. For example, when the first identification result indicates the "abnormal state", the first weight is 0.3, the second identification result indicates the "normal state", and the second weight is 0.7, a presenting identification result indicating that the tissue is in the "normal state" and that the reliability of this result is 70% can be presented.

More specifically, in step S404, the identification section 150 performs a process of determining the type of the organ in a tissue image, and weights the identification results based on the type of the organ thus determined.

Figures 26, 27:
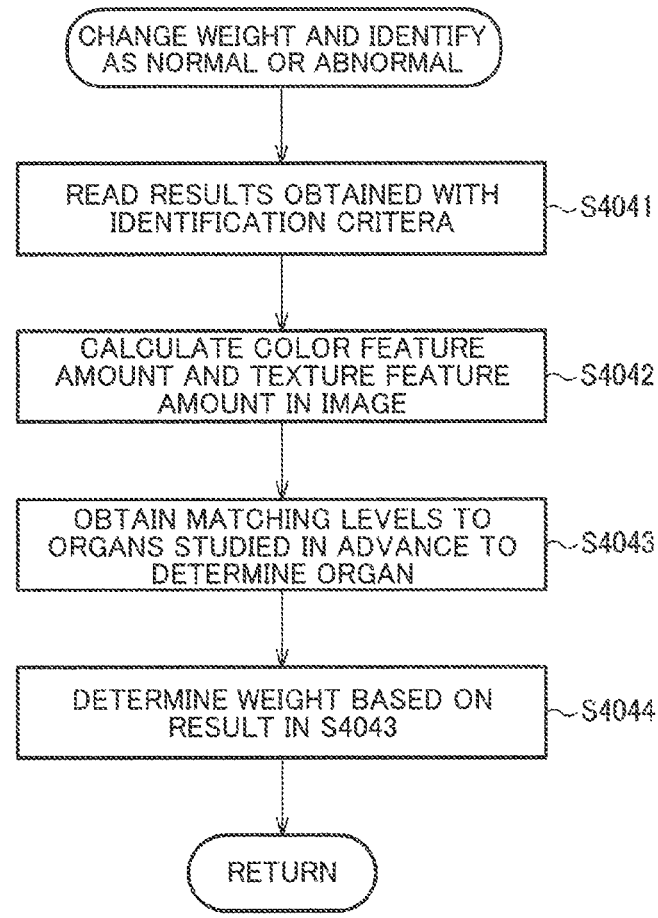
FIG. 26 is a flowchart illustrating a flow of a process for determining a weight provided to an identification result.
FIG. 27 is a diagram illustrating association between types of organs and weights provided to identification results.

FIG. 26 is a flowchart illustrating this process. The identification section 150 reads the results obtained by the identification criteria (S4041). Then, the processing section 130 calculates the color feature amount and the texture feature amount in the tissue image (S4042), and obtains the matching levels relative to the organs that have been learned in advance to determine the type of the organ (S4043). Then, the identification section 150 determines the weight based on a result of determining the organ (S4044).

Specifically, for example, table data indicating weights corresponding to the types of organs as illustrated in FIG. 27 is stored. Then, the weight corresponding to the type of the organ determined may be provided to the identification criteria. For example, as illustrated in FIG. 27, when the organ is the stomach, a weight of 0.2 is provided to an identification result obtained with an identification criterion A, a weight of 0.1 is provided to an identification result obtained with an identification criterion B, and a weight of 0.3 is provided to an identification result obtained with an identification criterion C. When the organ is the small intestine, a weight of 0.9 is provided to the identification result obtained with the identification criterion A, a weight of 0 is provided to the identification result obtained with the identification criterion B, and a weight of 0.1 is provided to the identification result obtained with the identification criterion C. The weights for other organs are provided in a similar manner.

Alternatively, in step S404, the identification section 150 may perform a process of acquiring patient information, and may weight an identification result based on the patient information thus acquired.

For example, this patient information is a purpose of the examination. Alternatively, the patient information may be acquired as a multi-dimensional feature amount that is a combination of pieces of information including the gender, age, condition, and the like of the patient.

Figure 28:
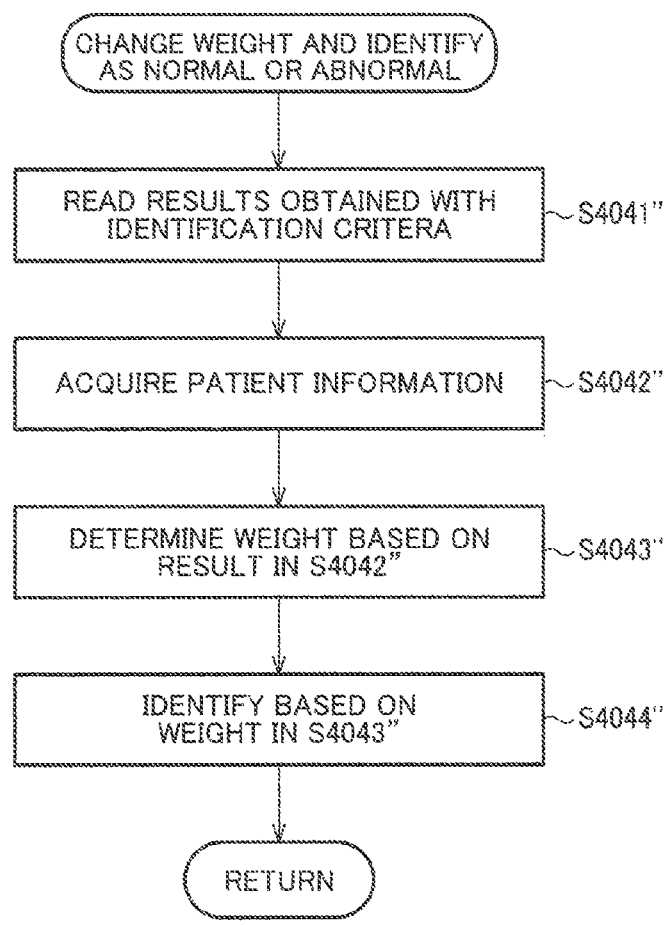
FIG. 28 is another flowchart illustrating a flow of a process for determining a weight provided to an identification result.

FIG. 28 is a flowchart illustrating a process in this case. The identification section 150 reads the results obtained with the identification criteria (S4041"), and acquires the patient information (S4042"). Next, the identification section 150 determines the weight of the identification result based on the patient information thus acquired (S4043"), and provides the weight to the identification result (S4044").

For example, when the purpose of the examination is screening, the main object of the examination would be to determine whether or not known abnormality is found. Thus, a large weight is provided to the identification result obtained with the corrected identification criterion. When the purpose of the examination is to identify the patient condition through detailed examination, the determination on whether or not the tissue is in an unknown abnormal state is important. Thus, a large weight is provided to the identification result obtained with the re-generated identification criterion.

Thus, the user can be notified of the importance of the identification result based on the type of the organ or the patient information, and the other like effect can be obtained.

The state of a tissue is less likely to suddenly change from the normal state to the abnormal state or from the abnormal state to the normal state, in the plurality of tissue images captured in time series. For example, when the state of the tissue in a tissue image captured at the current image capturing timing is determined to be the normal state, the state of the tissue in a tissue image captured at the next image capturing timing is likely to be determined to be the normal state.

Thus, the identification section 150 performs the identification process on the first tissue image in the plurality of tissue images captured in time series to obtain a first identification result, and performs the identification process on a second tissue image, in the plurality of tissue images, captured at the next image capturing timing to obtain the second identification result. The second identification result may be weighted based on the first identification result.

Figure 29:
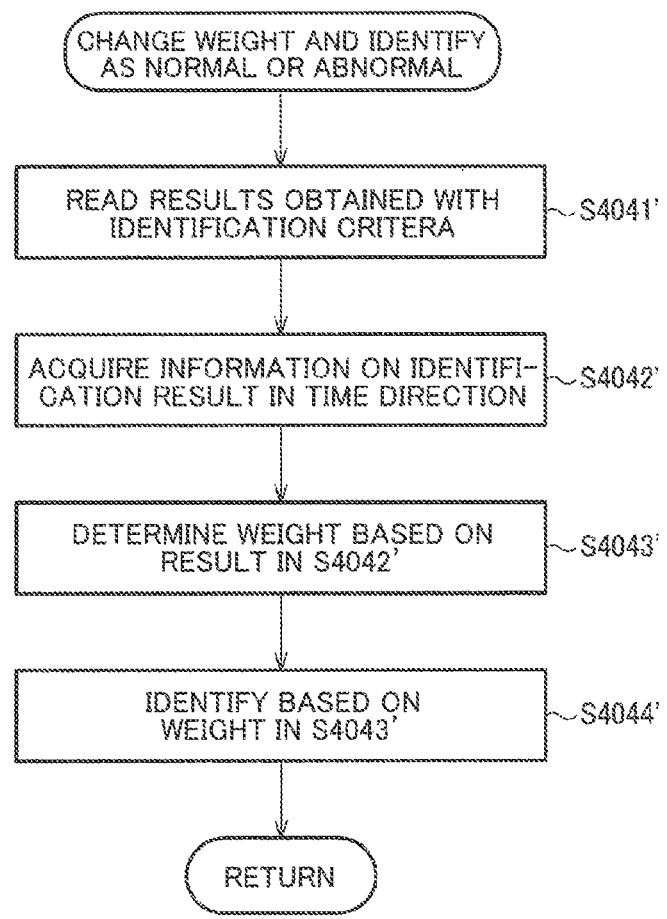
FIG. 29 is another flowchart illustrating a flow of a process for determining a weight provided to an identification result.

FIG. 29 is a flowchart illustrating this process. The identification section 150 reads the result obtained by the identification criterion (S4041'), and acquires information on the identification result in a time direction (S4042'). Next, the identification section 150 determines the weight for the identification result based on the information on the identification result in the time direction thus acquired (S4043'), and provides the weight to the identification result (S4044').

With this configuration, the identification accuracy can be improved in a case where the tissue images are acquired in time series and the other like effect cab be achieved.

7. Server System

In the example described above, the processing device 100 solely performs the process. However, the present embodiment is not limited to this. For example, the processing device 100 and an unillustrated server system, connected to the processing device 100 through a network, may cooperate to perform the process according to the present embodiment.

An identification criterion generated by the processing device 100 may be uploaded to the server system, and downloaded by another processing device, from the server system, to be used for the identification process.

In this configuration, the processing device 100 according to the present embodiment includes an unillustrated communication section that performs a process of transmitting the identification criterion generated and the property of a tissue image identified, to an external information processing device.

Thus, the identification criterion generated can be used by the other processing device, and the other like effect can be achieved.

The processes of the processing device or the like according to the present embodiment may be partially or mainly implemented with a program. In such a configuration, the processing device and the like according to the present embodiment are implemented when a processor such as a CPU executes the program. Specifically, a program stored in a non-transitory information storage device is read out and is executed by the processor such as a CPU. The information storage device (computer-readable device) stores a program and data, and has functions that can be implemented by an optical disk (e.g., CD-ROM and DVD), a hard disk drive (HDD), or a memory (e.g., memory card and ROM). The processor such as a CPU performs various processes according to the present embodiment based on a program (data) stored in the information storage device. Thus, the information storage device stores a program for causing a computer (a device including an operation section, a processing section, a storage section, and an output section) to function as each section according to the present embodiment (program for causing the computer to execute processes of each section).

The processing device or the like according to the present embodiment may include a processor and a memory. The processor may be a CPU, for example. Various other processors such as a graphics processing unit (GPU) or a digital signal processor (DSP) may also be used. The processor may be a hardware circuit that includes an ASIC. The memory stores a computer-readable instruction. Each section of the processing device and the like according to the embodiments of the invention is implemented by causing the processor to execute the instruction. The memory may be a semiconductor memory (e.g., a Static Random Access Memory (SRAM) or a Dynamic Random Access Memory (DRAM)), a register, a hard disk, or the like. The instruction may be an instruction included in an instruction set that is included in a program, or may be an instruction that causes a hardware circuit included in the processor to operate.

Although only some embodiments of the present invention and the modifications thereof have been described in detail above, those skilled in the art will readily appreciate that many modifications are possible in the embodiments without materially departing from the novel teachings and advantages of the invention. Accordingly, all such modifications are intended to be included within scope of the invention. For example, any term cited with a different term having a broader meaning or the same meaning at least once in the specification and the drawings can be replaced by the different term in any place in the specification and the drawings. The configurations and the operations of the processing device, the processing method, and a program are not limited to those described above in connection with the embodiments. Various modifications and variations may be made of those described above in connection with the embodiments.

What is claimed is:

1. A processing device comprising:
a processor comprising hardware, the processor being configured to:
acquire a tissue image obtained by capturing an image of a tissue;
determine a property of the tissue image acquired, and setting a plurality of identification criteria for identifying a state of the tissue as a normal state or an abnormal state, based on the tissue image and the property of the tissue image;
in response to the property of the tissue image being a first property, generate a re-generated identification criterion based on the tissue image and set the plurality of identification criteria to include an original identification criterion and the re-generated identification criterion; and in response to the property of the tissue image being a second property, correct the original identification criterion based on the tissue image to generate a corrected identification criterion and set the plurality of identification criteria to include the original identification criterion and the corrected identification criterion.

2. The processing device as defined in claim 1,
wherein the first property indicates the state of the tissue in the tissue image is an unknown abnormal state.

3. The processing device as defined in claim 1,
wherein the second property indicates the state of the tissue in the tissue image is a known abnormal state.

4. The processing device as defined in claim 1,
wherein the first property indicates an organ in the tissue image is a first organ, and
wherein the first property indicates the organ in the tissue image is a second organ.

5. The processing device as defined in claim 4,
the first organ being a non-examination target organ,
the second organ being an examination target organ.

6. The processing device as defined in claim 1,
wherein the processor is further configured to acquire additional information associated with the tissue image, and determine the property of the tissue image based on the additional information acquired.

7. The processing device as defined in claim 1,
wherein the processor is further configured to:
acquire a learning image appended with a true label indicating that the state of the tissue is the normal state or the abnormal state, and a test image not appended with the true label,
determine a property of the learning image, and set the plurality of identification criteria based on the learning image and the property of the learning image, and
identify the state of the tissue in the test image to be the normal state or the abnormal state based on the plurality of identification criteria.

8. The processing device as defined in claim 1,
wherein the processor is further configured to identify the state of the tissue in an identification accuracy calculation image, based on an identification criterion, as the normal state or the abnormal state, and calculate an identification accuracy obtained with the identification criterion.

9. The processing device as defined in claim 8,
wherein the processor is further configured to:
correct an original identification criterion based on the tissue image to obtain a corrected identification criterion,
obtain the identification accuracy obtained with the corrected identification criterion, and
set the corrected identification criterion to be one of the plurality of identification criteria, when the second property indicates that the identification accuracy obtained with the corrected identification criterion is equal to or higher than a given accuracy.

10. The processing device as defined in claim 8,
wherein the processor is further configured to generate a re-generated identification criterion and setting the re-generated identification criterion to be one of the plurality of identification criteria, when the first property indicates that the identification accuracy obtained with the corrected identification criterion is lower than a given accuracy.

11. The processing device as defined in claim 1,
wherein the processor is further configured to generate a new tissue image based on the tissue image acquired, and generate the re-generated identification criterion based on the original tissue image and the new tissue image generated.

12. The processing device as defined in claim 1,
wherein the processor is further configured to generate the re-generated identification criterion by increasing a weight of a feature amount of the tissue image acquired, in a feature amount distribution of an original identification criterion.

13. The processing device as defined in claim 1,
wherein the processor is further configured to select a feature amount distribution space of the re-generated identification criterion to generate the re-generated identification criterion.

14. The processing device as defined in claim 1,
wherein the processor is further configured to perform a limiting process for the correction of the original identification criterion and the generation of the corrected identification criterion.

15. The processing device as defined in claim 14,
wherein the limiting process is a process of reducing the weight for the feature amount of the tissue image in the feature amount distribution of the original identification criterion or a process of limiting a range of correcting the original identification criterion in the feature amount distribution space of the original identification criterion.

16. The processing device as defined in claim 1,
wherein the processor is further configured to identify the state of the tissue as the normal state or the abnormal state, based on the plurality of identification criteria set by the processor.

17. The processing device as defined in claim 16,
wherein the processor is further configured to identify the state of the tissue on a first tissue image in a plurality of tissue images obtained by capturing images of the tissue in time series, to obtain a first identification result,
identify the state of the tissue on a second tissue image in the plurality of tissue images to obtain a second identification result, the second tissue image being captured at an image capturing timing subsequent to an image capturing timing for the first tissue image, and
weighting the second identification result based on the first identification result.

18. The processing device as defined in claim 1,
wherein the processor is further configured to perform a process of transmitting the identification criterions set by the processor and the property of the tissue image determined to an external information processing device.

19. A processing method comprising:
acquiring a tissue image obtained by capturing an image of a tissue;
determining a property of the tissue image acquired;
setting a plurality of identification criteria for identifying a state of the tissue as a normal state or an abnormal state, based on the tissue image and the property of the tissue image;
in response to the property of the tissue image being a first property, generating a re-generated identification criterion based on the tissue image and setting the plurality of identification criteria to include an original identification criterion and the re-generated identification criterion; and in response to the property of the tissue image being a second property, correcting the original identification criterion based on the tissue image to generate a corrected identification criterion and setting the plurality of identification criteria to include the original identification criterion and the corrected identification criterion.

20. A computer-readable storage device with an executable program stored thereon, wherein the program instructs a microprocessor to perform the following steps of;

acquiring a tissue image obtained by capturing an image of a tissue; and determining a property of the tissue image acquired;

setting a plurality of identification criteria for identifying a state of the tissue as a normal state or an abnormal state, based on the tissue image and the property of the tissue image;

in response to the property of the tissue image being a first property, generating a re-generated identification criterion based on the tissue image and setting the plurality of identification criteria to include an original identification criterion and the re-generated identification criterion; and in response to the property of the tissue image being a second property, correcting the original identification criterion based on the tissue image to generate a corrected identification criterion and setting the plurality of identification criteria to include the original identification criterion and the corrected identification criterion.

21. A processing device comprising:

a processor comprising hardware, the processor being configured to:

acquire a tissue image obtained by capturing an image of a tissue;

determine a property of the tissue image acquired, and setting a plurality of identification criteria for identifying a state of the tissue as a normal state or an abnormal state, based on the tissue image and the property of the tissue image;

identify the state of the tissue as the normal state or the abnormal state based on an original identification criterion, included in the plurality of identification criteria set by the processor, to obtain a first identification result;

provide a first weight to the first identification result; and identify the state of the tissue as the normal state or the abnormal state based on one of a corrected identification criterion and a re-generated identification criterion, included in the plurality of identification criteria set by the processor, to obtain a second identification result; and provide a second weight to the second identification result.

22. The processing device as defined in claim 21, wherein the processor is further configured to obtain a presenting identification result to be presented to a user, based on the first identification result provided with the first weight and the second identification result provided with second weight.

23. The processing device as defined in claim 21, wherein the processor is further configured to determine a type of an organ in the tissue image or acquire patient information, and weight an identification result based on the type of the organ determined or the patient information acquired.

24. A processing device comprising:

a processor comprising hardware, the processor being configured to:

acquire a tissue image obtained by capturing an image of a tissue;

determine a property of the tissue image acquired, and setting a plurality of identification criteria for identifying a state of the tissue as a normal state or an abnormal state, based on the tissue image and the property of the tissue image;

in response to an organ in the tissue image being a first organ, generate a re-generated identification criterion based on the tissue image and set the plurality of identification criteria to include an original identification criterion and the re-generated identification criterion; and in response to an organ in the tissue image being a second organ, correct the original identification criterion based on the tissue image to generate a corrected identification criterion and set the plurality of identification criteria to include the original identification criterion and the corrected identification criterion.

25. A processing device comprising:

a processor comprising hardware, the processor being configured to:

acquire a tissue image obtained by capturing an image of a tissue;

determine a property of the tissue image acquired, and setting a plurality of identification criteria for identifying a state of the tissue as a normal state or an abnormal state, based on the tissue image and the property of the tissue image;

identify the state of the tissue in an identification accuracy calculation image, based on an identification criterion, as the normal state or the abnormal state, and calculate an identification accuracy obtained with the identification criterion;

correct an original identification criterion based on the tissue image to obtain a corrected identification criterion;

obtain the identification accuracy obtained with the corrected identification criterion;

setting the corrected identification criterion to be one of the plurality of identification criteria, when the identification accuracy obtained with the corrected identification criterion is equal to or higher than a given accuracy; and generate a re-generated identification criterion and set the re-generated identification criterion to be one of the plurality of identification criteria, when the identification accuracy obtained with the corrected identification criterion is lower than the given accuracy.

* * * * *